United States Patent
Marcil

(10) Patent No.: US 11,141,109 B2
(45) Date of Patent: Oct. 12, 2021

(54) BITE FORCE MEASURING SYSTEM AND MOUTHPIECE

(71) Applicant: Kube Innovation Inc., Montreal (CA)

(72) Inventor: Frederik Marcil, Lachine (CA)

(73) Assignee: KUBE INNOVATION INC., Montreal (CA)

( * ) Notice: Subject to any disclaimer, the term of this patent is extended or adjusted under 35 U.S.C. 154(b) by 72 days.

(21) Appl. No.: 16/622,974

(22) PCT Filed: Jun. 22, 2018

(86) PCT No.: PCT/CA2018/050768
§ 371 (c)(1),
(2) Date: Dec. 16, 2019

(87) PCT Pub. No.: WO2019/000081
PCT Pub. Date: Jan. 3, 2019

(65) Prior Publication Data
US 2020/0155067 A1    May 21, 2020

Related U.S. Application Data

(60) Provisional application No. 62/525,800, filed on Jun. 28, 2017.

(51) Int. Cl.
*A61B 5/00* (2006.01)
*A61B 5/22* (2006.01)

(52) U.S. Cl.
CPC ............ *A61B 5/682* (2013.01); *A61B 5/0002* (2013.01); *A61B 5/228* (2013.01);
(Continued)

(58) Field of Classification Search
CPC ........ A61B 5/228; A61B 5/682; A61C 9/0006
See application file for complete search history.

(56) References Cited

U.S. PATENT DOCUMENTS 4,976,618 A    12/1990  Anderson
5,720,293 A *  2/1998  Quinn .................... A61B 5/028
                                                                  600/505
(Continued)

FOREIGN PATENT DOCUMENTS

EP    2135552 A1    12/2009
EP    2742920 A1    6/2014

OTHER PUBLICATIONS

Alibrahim et al. The Measurement of Maximal Bite Force in Human Beings, 2015, University of Dundee (Year: 2015).*

*Primary Examiner* — Eric F Winakur
*Assistant Examiner* — Jasim Ahmad Naeem
(74) *Attorney, Agent, or Firm* — IP Delta Plus Inc.

(57) ABSTRACT

A bite force measuring system comprising a mouthpiece interfaced to a control unit. The mouthpiece comprises memory for storing calibration parameters. The mouthpiece comprises a fluid-filled compressible cavity, and a fluid-pressure-sensing device for measuring a pressure of a fluid contained in the fluid-filled compressible cavity. The mouthpiece comprises a communication interface for transmitting the calibration parameters and the measured pressure to the control unit. The control unit comprises a communication interface for receiving the calibration parameters and the measured pressure from the mouthpiece. The control unit comprises a processing unit for calculating a bite force corresponding to the measured pressure. The calibration parameters and the measured pressure are used calculating the bite force corresponding to the measured pressure. The calibration parameters may consist of coefficients of a polynomial equation for calculating the bite force by applying the polynomial equation to the measured pressure. A calibration method is also disclosed.

18 Claims, 13 Drawing Sheets

(52) U.S. Cl.
CPC ............ *A61B 2560/0223* (2013.01); *A61B 2562/0247* (2013.01); *A61B 2562/164* (2013.01)

(56) References Cited

U.S. PATENT DOCUMENTS

| | | |
|---|---|---|
| 5,846,211 A | 12/1998 | Sakaguchi et al. |
| 6,190,335 B1 | 2/2001 | Howard et al. |
| 6,786,092 B2 | 9/2004 | Nakao |
| 6,993,954 B1 | 2/2006 | George et al. |
| 2007/0235231 A1 | 10/2007 | Loomis et al. |
| 2012/0123225 A1 | 5/2012 | Al-Tawil |
| 2013/0211270 A1* | 8/2013 | St. Laurent .......... A61B 5/4875 600/508 |

\* cited by examiner

BITE FORCE MEASURING SYSTEM AND MOUTHPIECE

TECHNICAL FIELD

The present disclosure relates to the field of medical diagnostic. More specifically, the present disclosure relates to a system for measuring a bite force of an individual comprising a mouthpiece interfaced to a control unit, and a method for calibrating the mouthpiece.

BACKGROUND

Measuring the bite force in a patient is used as a screening tool in the everyday practice of dental professionals across the world. For example, measuring the bite force in a patient is often required to evaluate dental health of patients and diagnose or prevent different dysfunctions, pathologies or diseases. For instance, unbalanced dental occlusion may be associated to different pathologies and should be detected and quantified to enable appropriate therapeutic undertaking. It may be further involved in the treatment of bruxism and temporomandibular joint dysfunction and the like. Measurement of other intraoral forces involved in mastication such as forces applied by the tongue or cheek muscles may also be useful.

A variety of devices and systems are currently used to assist health care professionals such as dentists, denturists and physiotherapists in measuring a force exerted between teeth or a pressure or average force applied by the jaws. Some devices are devised for the local measurement of a force between a pair of opposite upper and lower teeth, but are not capable of providing information about the average bite force. Certain devices and systems employ mechanical gauges that provide inaccurate measurements and are not capable of detecting nor quantifying an unbalance between left side and right side occlusion.

Systems employing resistive or piezoelectric sensor equipped mouthpieces enable oro-myographic measurements and provide a mapping of contact forces for detailed analysis of dental occlusion. Such devices and systems are expensive, do not provide direct measurement of the bite force and use single patient disposable sensing mouthpieces further increasing operation costs.

Some devices and systems rely on mouthpieces having fluid filled compressible cavities to provide indication of oral pressures and forces. While those systems and devices may enable measurement of a bite force, they nevertheless fail to provide a simple, reliable, accurate and practical solution, having long runs of flex tubing or a rigid connection extending between the sensing mouthpiece and the controlling/displaying unit. They also generally lack features for properly aligning the mouthpiece on the teeth and for enabling repeated uses in different patients without requiring replacement or sterilization of the mouthpiece.

Furthermore, most of the devices and systems for measuring a bite force need to be calibrated before usage. The calibration procedure is generally complex and may involve a great deal of human intervention and expertise.

Therefore, advances in the field of maxillofacial health diagnostic, dental occlusion analysis and bite force measurement may be achieved by improving the accuracy, user friendliness and cost-effectiveness of devices and systems for measuring a bite force of a patient.

There is therefore a need for a new system for measuring a bite force of an individual comprising a mouthpiece interfaced to a control unit.

SUMMARY

According to a first aspect, the present disclosure relates to a mouthpiece adapted for being interfaced with a control unit. The mouthpiece comprises memory for storing calibration parameters. The mouthpiece comprises a fluid-filled compressible cavity, and a fluid-pressure-sensing device for measuring a pressure of a fluid contained in the fluid-filled compressible cavity. The mouthpiece comprises a communication interface for transmitting the calibration parameters and the measured pressure to the control unit. The calibration parameters and the measured pressure are used by the control unit for the calculation of a bite force corresponding to the measured pressure.

According to a second aspect, the present disclosure relates to a bite force measuring system comprising a mouthpiece interfaced to a control unit. The mouthpiece comprises memory for storing calibration parameters. The mouthpiece comprises a fluid-filled compressible cavity, and a fluid-pressure-sensing device for measuring a pressure of a fluid contained in the fluid-filled compressible cavity. The mouthpiece comprises a communication interface for transmitting the calibration parameters and the measured pressure to the control unit. The control unit comprises a communication interface for receiving the calibration parameters and the measured pressure from the mouthpiece. The control unit comprises a processing unit for calculating a bite force corresponding to the measured pressure. The calibration parameters and the measured pressure are used for the calculation of the bite force corresponding to the measured pressure.

According to a third aspect, the present disclosure relates to a method for calibrating a mouthpiece comprising a fluid-filled compressible cavity. The method comprises repeating the following three steps a plurality of times. A first step consisting in applying a load on a body of the mouthpiece to exert a force on a fluid contained in the fluid-filled compressible cavity. A second step consisting in measuring, by a fluid-pressure-sensing device of the mouthpiece, a pressure of a fluid contained in the fluid-filled compressible cavity. A third step of transmitting the value of the exerted force and the measured pressure to a computing device. The method further comprises determining, by a processing unit of the computing device, calibration parameters of the mouthpiece based on the values of the plurality of exerted forces and the corresponding plurality of measured pressures. The calibration parameters allow the calculation of a bite force based on the calibration parameters and a corresponding measured pressure. The method comprises transmitting the calibration parameters from the computing device to the mouthpiece. The method comprises storing the calibration parameters in a memory of the mouthpiece.

According to a particular aspect, the calibration parameters consist of coefficients of a polynomial equation of degree N with N greater or equal than 1, the bite force corresponding to the measured pressure being calculated by applying the polynomial equation to the measured pressure.

According to another particular aspect, the polynomial equation is of degree 2 and the calibration parameters consist of three coefficients a, b, and c; the bite force $F_{cal}$ corresponding to the measured pressure x being calculated as follows: $F_{cal} = ax^2 + bx^1 + c$.

BRIEF DESCRIPTION OF THE DRAWINGS

Embodiments of the disclosure will be described by way of example only with reference to the accompanying drawings, in which:

FIG. 2b is a perspective view of a fluidic tubing network of the mouthpiece of FIG. 2a;

FIG. 3 is a cross sectional view taken along line 3-3 of a body portion of the mouthpiece of FIG. 2a;

FIG. 4c is a top view of the mouthpiece of FIG. 2a;

FIG. 6a represents a control/display unit of the system of FIG. 1, displaying information when using a single cavity mouthpiece according to FIG. 4a;

DETAILED DESCRIPTION

The foregoing and other features will become more apparent upon reading of the following non-restrictive description of illustrative embodiments thereof, given by way of example only with reference to the accompanying drawings. Like numerals represent like features on the various drawings.

Various aspects of the present disclosure generally address one or more of the problems related to the measurement of a bite force of an individual by a system comprising a mouthpiece, the mouthpiece being adapted for measuring a pressure applied by one or more tooth of the individual on the mouthpiece, the bite force being calculated based on the measured pressure.

The following terminology is used throughout the present disclosure:

Intraoral force: a force applied by an organ of an intraoral cavity, such as a force applied by a tongue, a force applied by the masseter or other masticatory muscles, a force applied by one or more teeth of a jaw, etc.

Bite force: a particular type of intraoral force consisting of a force applied by one or more teeth of a jaw.

Occlusion balance: relative force between the left and the right side of the jaw measured simultaneously.

Figure 1:
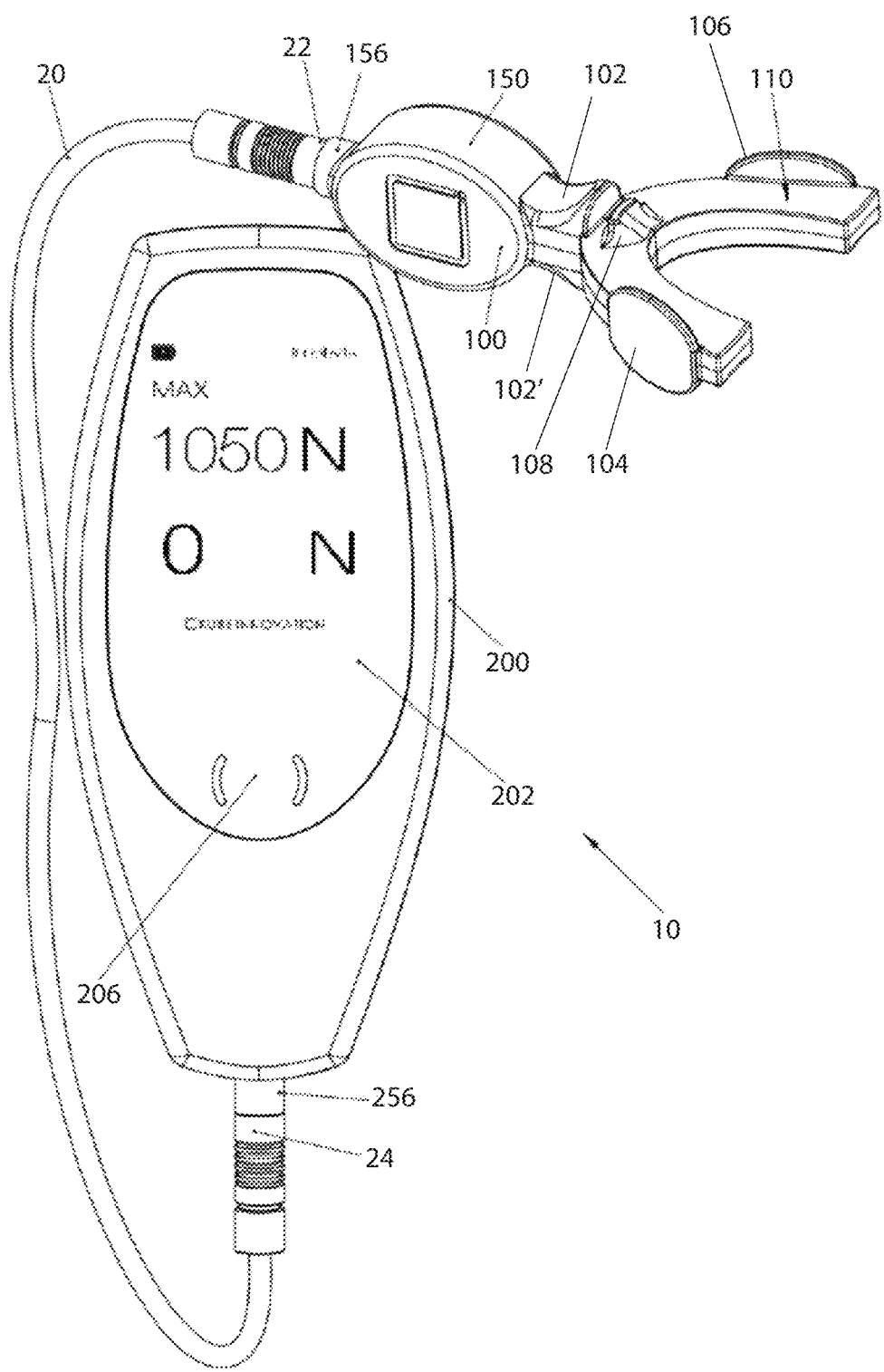
FIG. 1 is a general perspective representation of a bite force measuring system.

Referring now to FIG. 1, there is shown a bite force measuring system 10, comprising a mouthpiece 100 linked and connected to a compact hand-held control and display unit 200 through a flexible electrical cable assembly 20. The electrical cable assembly 20 comprises electrical connectors 22 and 24 to enable removable electrical connection between the mouthpiece 100 and the control/display unit 200. Alternatively, the mouthpiece 100 and the control/display unit 200 are not physically linked to one another; but are connected through a wireless connection (not represented in FIG. 1) allowing exchange of information there between using wireless communication protocol(s). The mouthpiece 100 is devised for being partly inserted into an intraoral cavity of an individual and to be submitted to a bite force applied thereon by the individual's teeth. Compression of the inserted portion of the mouthpiece increases a pressure of a fluid therein, the pressure increase being converted into an electrical signal directly into the mouthpiece, the signal being transmitted to the control unit 200 through the cable 20 (or alternatively wirelessly) to be processed by the control unit 200 and for displaying a reading indicative of the measured bite force and/or pressure on display 202. User interface 206 (e.g. a capacitive switch) is provided to enable control, such as powering ON/OFF and operating mode selection.

Figure 2A:
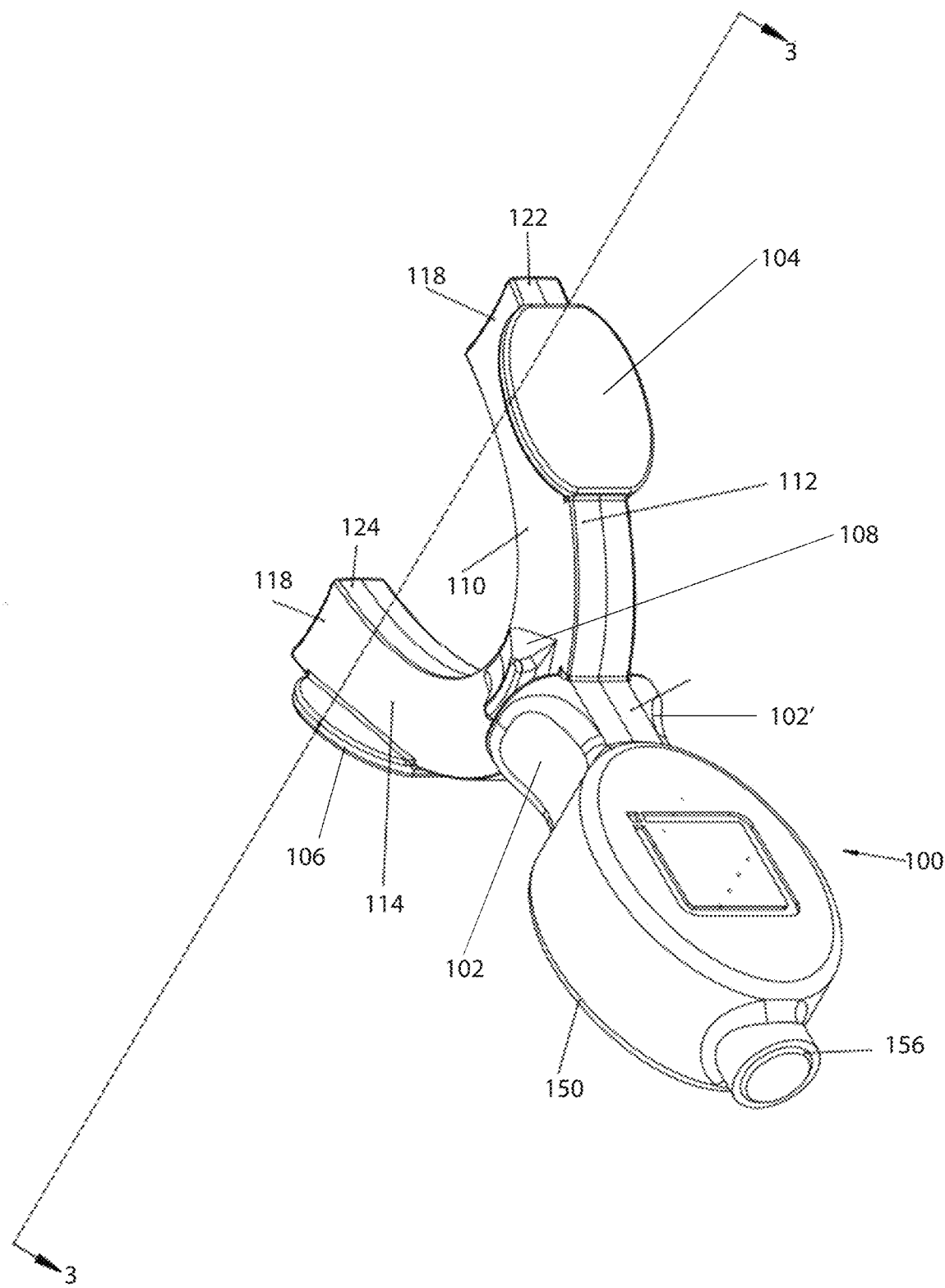
FIG. 2a is a perspective view of a mouthpiece of the system of FIG. 1.
Figure 2B:
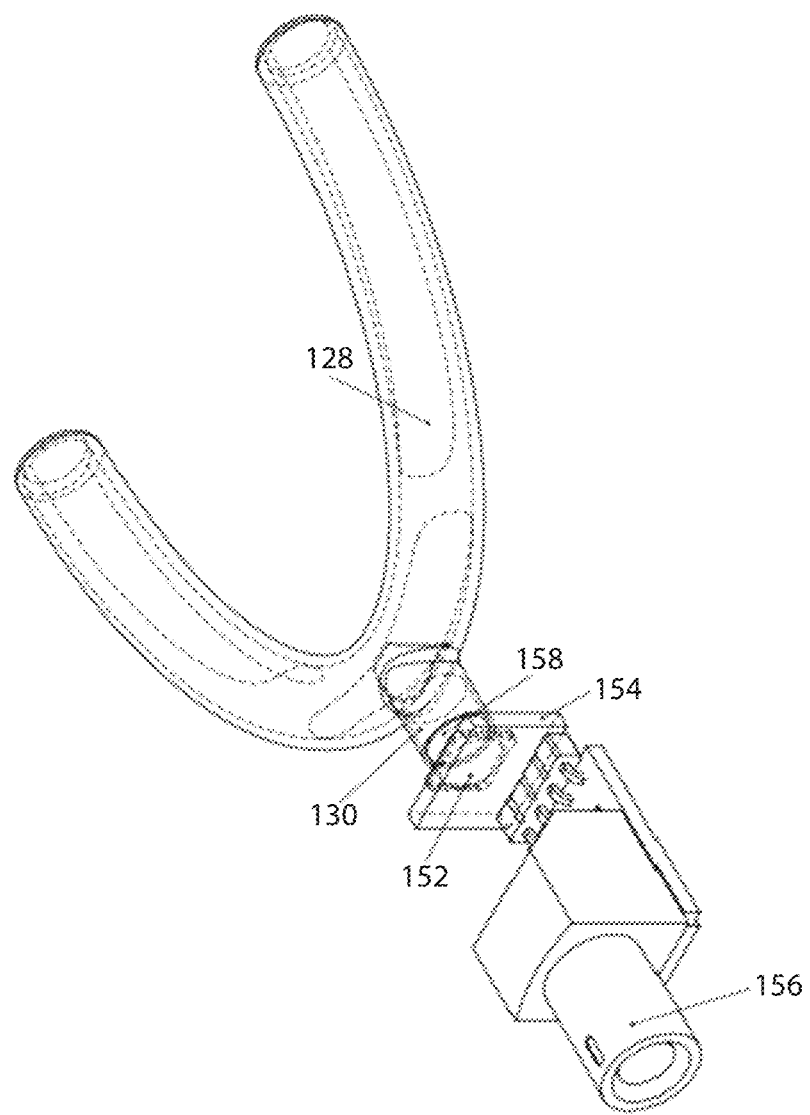

Reference is now made concurrently to FIGS. 2a, 2b, 3 and 4. FIG. 2a represents the mouthpiece 100 comprising a generally horseshoe shaped body 110 defining a first branch 112 and a second branch 114 intersecting at a fore end 116. The body 110 is the portion of the mouthpiece 100 that is adapted for insertion and positioning between upper and lower teeth into an intraoral cavity. The mouthpiece 100 further comprises a sensor compartment 150 attached and projecting from the fore end 116 for housing a fluid-pressure-sensing device 152 (represented in FIG. 4a).

Figure 3:
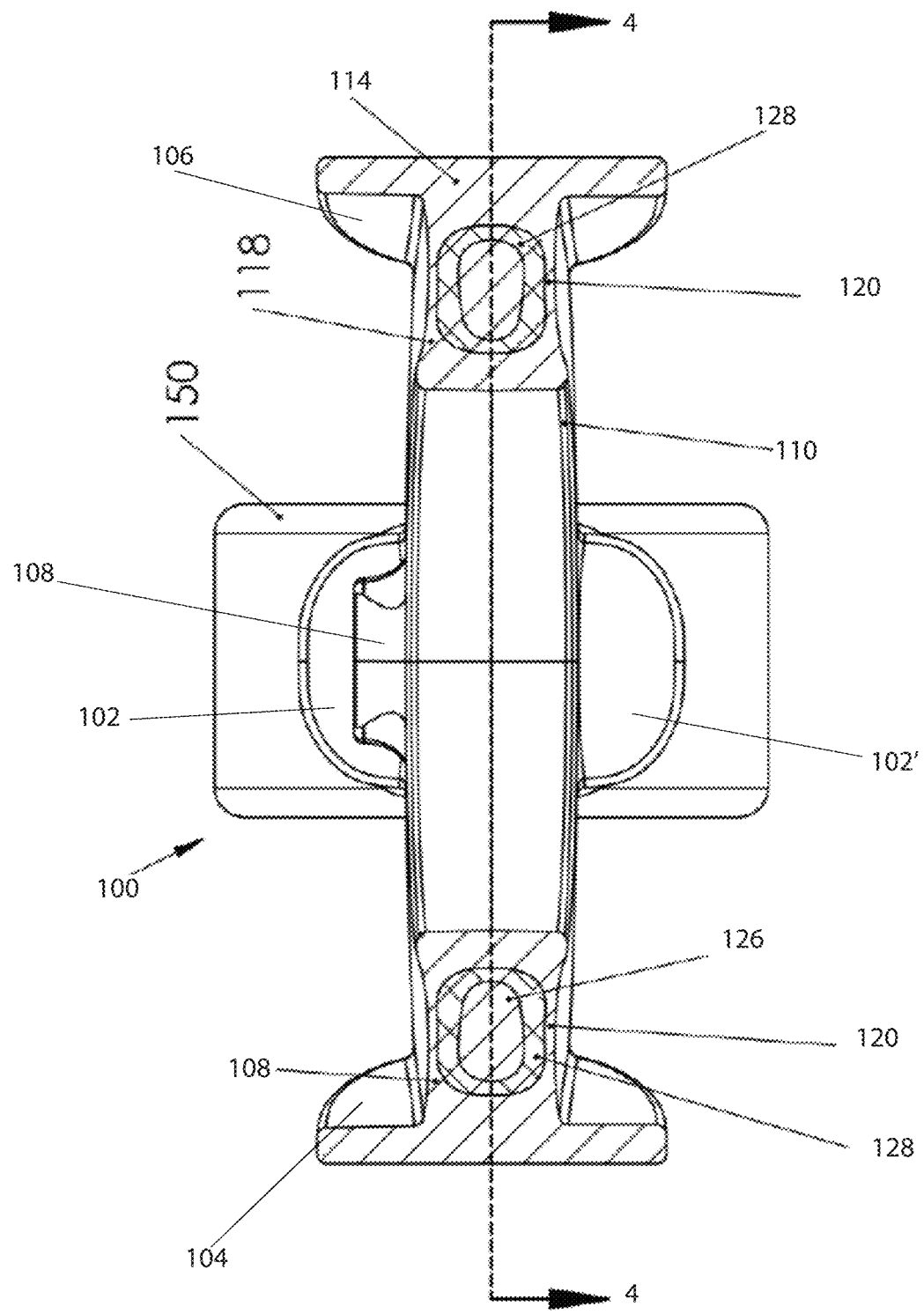

FIG. 3 represents a detailed view of a portion of the body 110 of the mouthpiece 100, showing the concave shaped cross section defined by upper and lower recessed channels 118 and 120. The dimensioning and shaping of the body 110 are adapted to enable stable insertion between upper and lower teeth of a typical individual. Channels 118 and 120 improve alignment and retention of the body in a proper position between the teeth. Proportionally larger and smaller models may be provided to adapt to individuals having a substantially larger or smaller intraoral cavity than the average individual.

Other shapes and dimensions of the body 110 may also be contemplated should measurement of other forces and pressures of the intraoral cavity be contemplated. Still, advantages inherent to the integrated concept of the mouthpiece and other features of the system would remain prevalent.

Figure 4A:
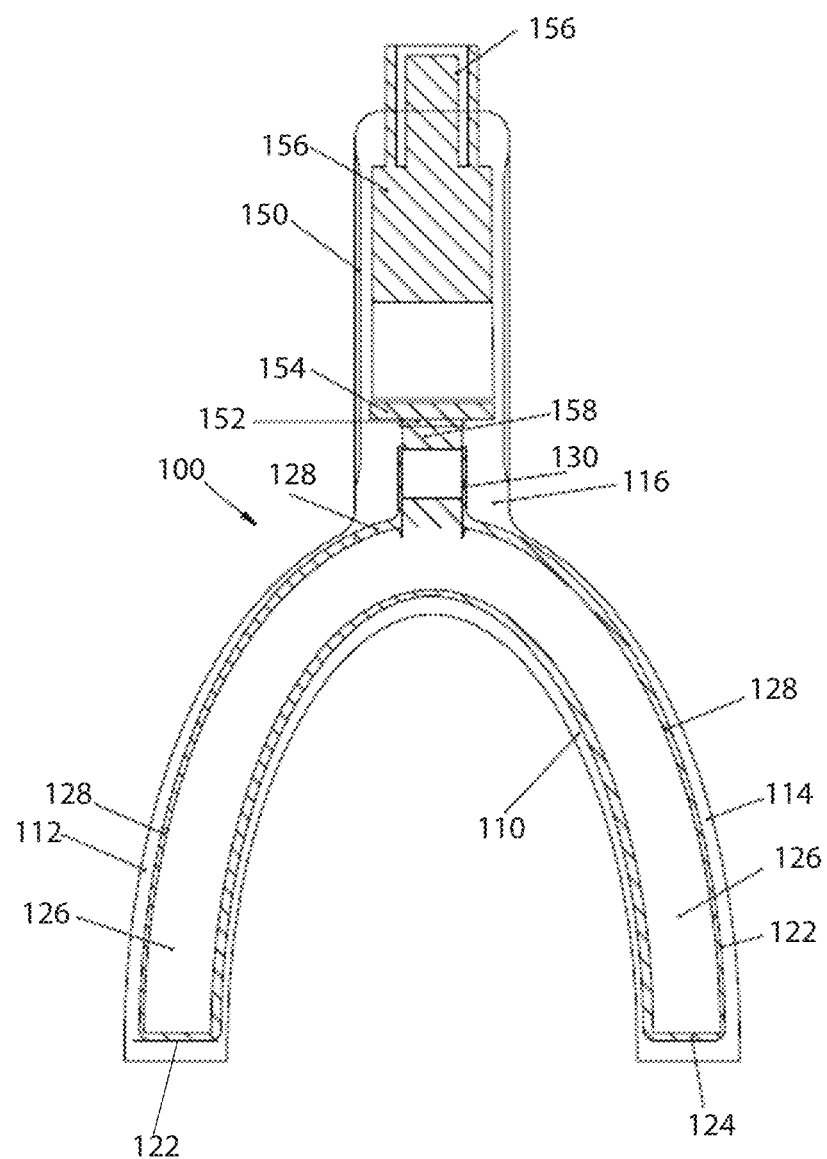
FIG. 4a is a top cross-sectional view of a mouthpiece of the system of FIG. 1, taken along line 4-4 of FIG. 3, having a single compressible cavity.

The body 110 further comprises a tubular inner cavity 126 adapted for receiving a fluid therein. This internal fluidic tubing network 128 is represented in FIGS. 3 and 4a. In the complete body, branches 112 and 114 are closed in a fluid tight manner at their back ends 122 and 124 to retain a compressed fluid therein, as illustrated by FIG. 4a. The body 110 is molded from a flexible and resilient material such as a silicon based elastomeric material, flexible plastic, another type of flexible material, etc.

Molding may be performed by overmolding of the silicon compound over a preassembled network of flexible tubing 128, to provide the compressible cavity or cavities 126, and fluidic connections. The internal tubing network 128 is filled with incompressible fluid such as water, vegetable oil or glycerin; and connected to a pressure sensor 152 (represented in FIG. 4a), prior to overmolding with the elastomeric compound into the final shape. Alternatively, a compressible fluid such as air may be used in the internal tubing network 128.

The body 110 has a Shore A hardness factor between 20 and 80, and preferably 40; which is appropriate to properly transfer a mechanical pressure applied by the teeth to a fluid contained into the compressible cavity 126. Furthermore, a Shore A hardness factor between 20 and 80 provides a correlation between the bite force applied by the teeth on the body 110, and the bite force measured by the system 10 (represented in FIG. 1). The correlation can be observed for bite forces in the range of 0 to 5000 Newtons. By comparison, existing systems having a Shore A hardness factor higher than the 20-80 range do not provide a correlation between the applied bite force and the measured bite force. The correlation can be of various types, such as a N degree (e.g. $2^{rd}$ degree) polynomial equation, etc.

Referring back to FIG. 2a, In a particular configuration, a section of the body 110 increases from the back ends 122 and 124 of the branches 112 and 114 towards the fore end 116. Thus, a section of the branches 112 and 114 is lower when closer to their respective back ends 122 and 124, and higher when farther from their respective back ends 122 and 124. The increase of the section may extend on the whole length of the branches 112 and 114, between their respective back ends 122 and 124 and the fore end 116. Alternatively, the increase of the section extends only partially along the branches 112 and 114, starting at their respective back ends 122 and 124 and ending at a maximum section located before the fore end 116.

The combination of the body 110 being molded from a silicon based elastomeric material (or flexible plastic) and having an increasing section (from the back ends 122 and 124 of the branches 112 and 114 towards the fore end 116) results in a reduction of the loss of the bite force applied by the jaw on the body 110, thus improving the accuracy of the measurement of the applied bite force.

In a particular configuration, the body 110 further comprises three guides for better positioning of the body 110 with respect to the jaw of the patient, and for maintaining the body 110 in position within the jaw of the patient while proceeding with a bite force measurement. One guide comprises two extensions 102 and 102' respectively located at the top and at the bottom of the fore end 116. The extensions 102 and 102' are used for positioning the lips of the patient. The two other guides 104 and 106 are respectively symmetrically secured to an external surface of the branches 112 and 114, in proximity of the back ends 122 and 124 of the branches 112 and 114; and respectively extend vertically. An additional guide 108 is located on top of the intersection of the branches 112 and 114. The guide 108 and the extension 102 face each other and provide a space therebetween for positioning and blocking the incisors of the patient between the guide 108 and the extension 102. At least some of the guides 102-102', 104-106 and 108 are present simultaneously on the mouthpiece 100; and contribute to the accuracy and repeatability of the measurement of the applied bite force. The guides 102, 102', 104, 106 and 108 are represented in FIGS. 1, 2a and 3. Furthermore, FIGS. 4c and 4d respectively provide a top view and a cross-sectional view of the mouthpiece 100, with the guides 102, 102', 104, 106 and 108 represented.

Figure 5:
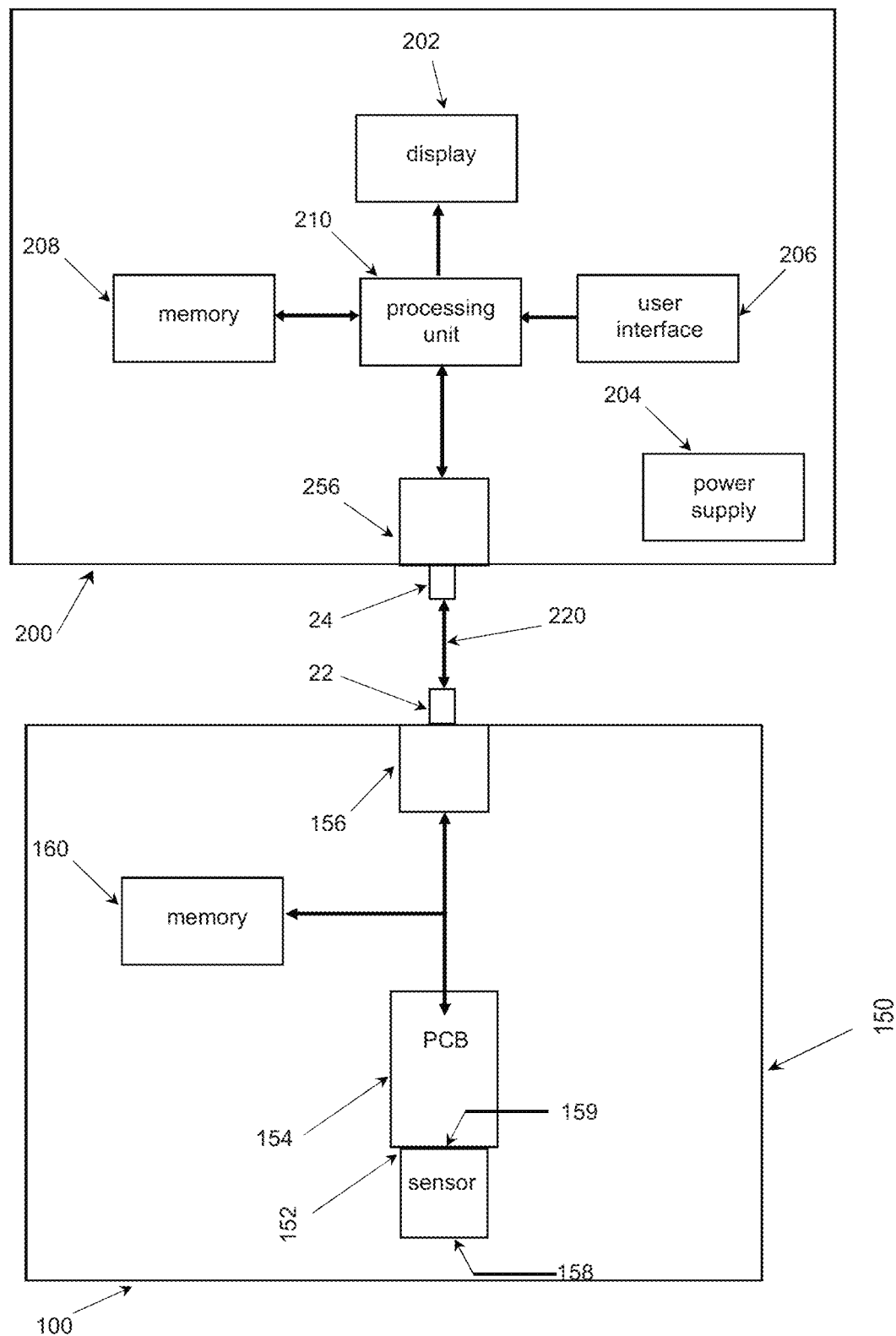
FIG. 5 is a schematic diagram of an internal architecture of a control and display unit of the system of FIG. 1.

Reference is now made concurrently to FIGS. 1, 4a and 5. FIG. 4a represents a cross sectional view of the complete mouthpiece 100 as viewed from the direction indicated by lines 4-4 in FIG. 3. The sealed flexible tubing network 128 has an open end 130 connected to the fluid-pressure-sensing device 152 mounted onto a printed circuit board (PCB) 154 housed in the compartment 150. The sensor 152 is a solid-state sensor electrically connected to a female electrical connector 156 molded in compartment 150. The female electrical connector 156 provides electrical connection between the PCB 154 and the control/display unit 200 through the mating male connector 22 and conductors in the electrical cable 20 (represented in FIG. 1). As illustrated in FIG. 5, the fluid pressure is applied at inlet 158 of the sensor 152, and an electrical signal representative of the pressure measured by the sensor 152 is generated at output 159 of the sensor 152. The output 159 of the sensor 152 is connected to the PCB 154. The representative electrical signal is transmitted by the PCB 154 to the control/display unit 200 through a digital communication link 220 provided by electrical connectors 156 and 256 and electrical conductors in cable 20 (represented in FIG. 1). Memory 160 (e.g. a solid-state memory device such as Flash or EPROM) is further mounted on the PCB 154, and connected to the communication link 220. Various types of memory 160 may be used for the mouthpiece 100. The memory 160 provides storage and retrieval of information specific to the mouthpiece 100 and/or sensor 152, such as identification information used by the control/display unit 200 to accordingly control operations performed by a software program executed on the control/display unit 200. For instance, the memory 160 stores information indicative of the size of the mouthpiece 100 being connected to the control/display unit 200. The mouthpieces 100 may be offered in different sizes such as small, medium and large size, to adapt to different oral cavities and teeth occlusions. To properly convert the fluid pressure measured by the sensor 152 and transmitted through the PCB 154 into a corresponding bite force, the control/display unit 200 needs to know which type of mouthpiece 100 is connected thereto. Furthermore, mouthpiece types include mouthpieces having a plurality (at least two) of separate fluid cavities and a corresponding plurality of pressure sensors, according to different configurations adapted for measuring a bite force at different locations of an oral cavity. Information allowing identification of the measured pressure values transmitted by each pressure sensor are also stored in the memory 160, as will be illustrated later in the description.

Additional information can be stored in the memory 160 of the mouthpiece 100, and transmitted to the control/display unit 200, initialized by the control/display unit 200, updated by the control/display unit 200, etc. The exchange of information between the memory 160 and the control/display unit 200 is performed at the initiative of the mouthpiece 100 or at the initiative of the control/display unit 200, depending on the type of information stored in memory 160. For example, a serial number for uniquely identifying the mouthpiece 100 is stored in the memory 160, and transmitted to the control/display unit 200 upon request by the control/display unit 200. The serial number is further displayed on a display of the control/display unit 200 for identifying the mouthpiece 100 currently connected to the control/display unit 200 (for traceability purposes). In another example, a number of measurement cycles is stored in the memory 160. The number of measurement cycles is initialized at a value of 0. The number of measurement cycles stored in the memory 160 is read and incremented by the control/display unit 200 for each determination of a pressure (and/or corresponding bite force) performed by the control/display unit 200 based on information transmitted by the mouthpiece 100. In an exemplary implementation, the measurement cycle is only incremented if the bite force is greater than a pre-defined threshold (e.g. 60 N). Once the number of measurement cycles reaches another pre-defined threshold (e.g. 1000 operations), a message is displayed on the display of the control/display unit 200 indicating that the maximum number of measurement cycles has been reached. In this case, the mouthpiece 100 should be disposed of, and replaced by a new mouthpiece. The pre-defined thresholds (e.g. 60 N and 1000 operations) are also stored in the memory 160; and may vary based on various types of mouthpieces being used. Alternatively, the pre-defined thresholds are stored in a memory of the control/display unit 200.

In an alternative configuration, instead of a wired communication interface comprising the female electrical connector 156, the PCB 154 includes a wireless communication interface (not represented in the Figures) providing wireless digital communication between the mouthpiece 100 and the control/display unit 200. The control/display unit 200 is also equipped with a wireless communication interface.

The mouthpiece 100 may also include a processing unit (not represented in the Figures) for controlling operations of the components (sensor 152, memory 160, etc.) of the mouthpiece 100, interacting with the processing unit 210 of the control/display unit 200, etc. The processing unit of the mouthpiece 100 is mounted on the PCB 154. For instance, when a wireless communication interface is used in place of the wired communication interface comprising the female electrical connector 156, the processing unit of the mouthpiece 100 is used for controlling the transfer of information (generated by the sensor 152, stored in the memory 160, etc.) between the mouthpiece 100 and the control/display unit 200 via the wireless communication interface of the mouthpiece 100.

Any type of pressure sensor 152 capable of converting a fluid pressure into a corresponding representative electrical signal can be used, provided that the pressure sensor is adapted for being mounted on the PCB 154 housed in the compartment 150. The electrical signal generated by the pressure sensor is preferably digital. However, in the case of an analog electrical signal, an analog to digital (ADC) converter mounted on the PCB 154 or 154' converts the analog electrical signal into a corresponding digital electrical signal, which is transmitted to the control/display unit 200.

Figure 4B:
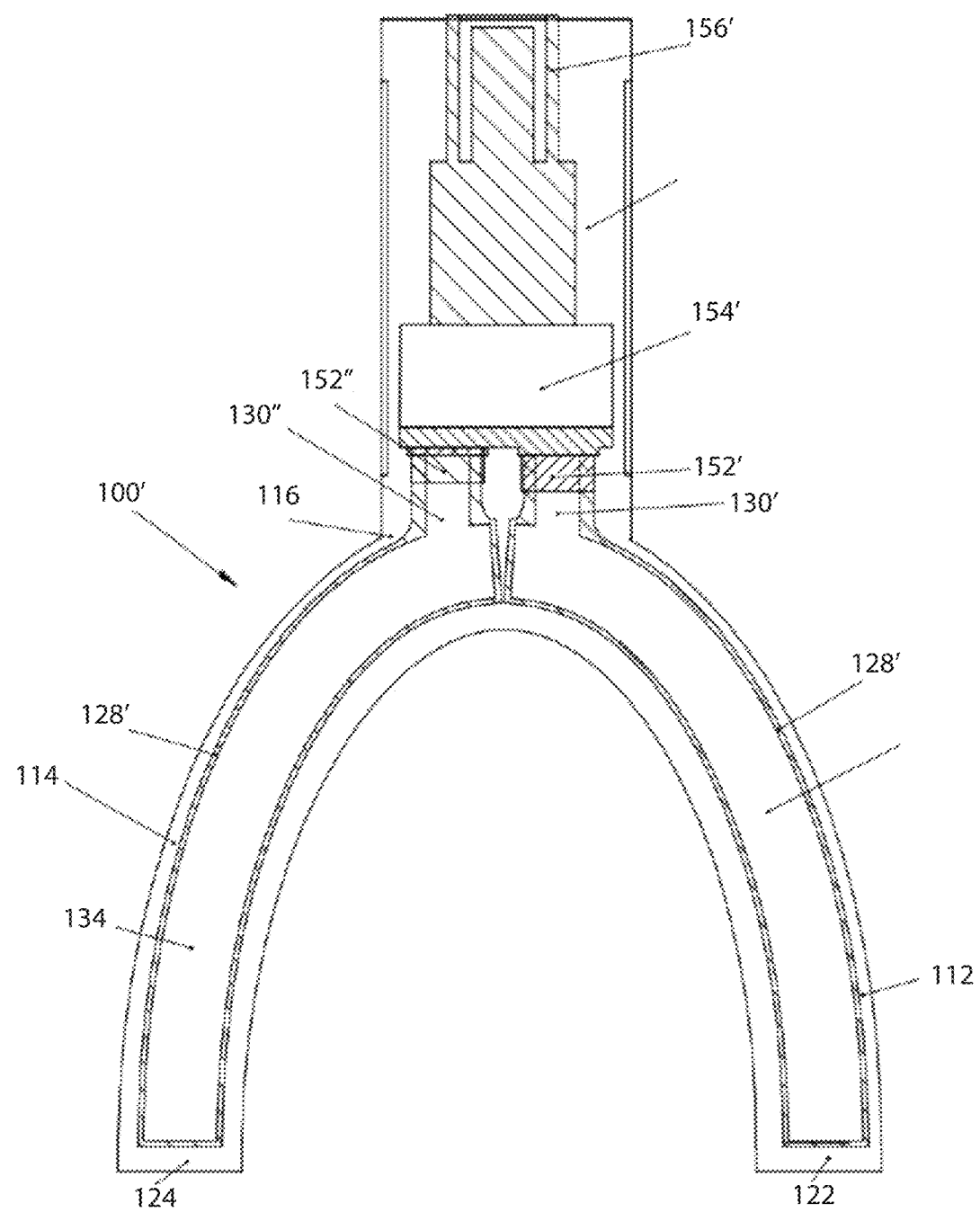
FIG. 4b is a top cross-sectional view of a mouthpiece of the system of FIG. 1, having two symmetrical compressible cavities.
Figure 4C:
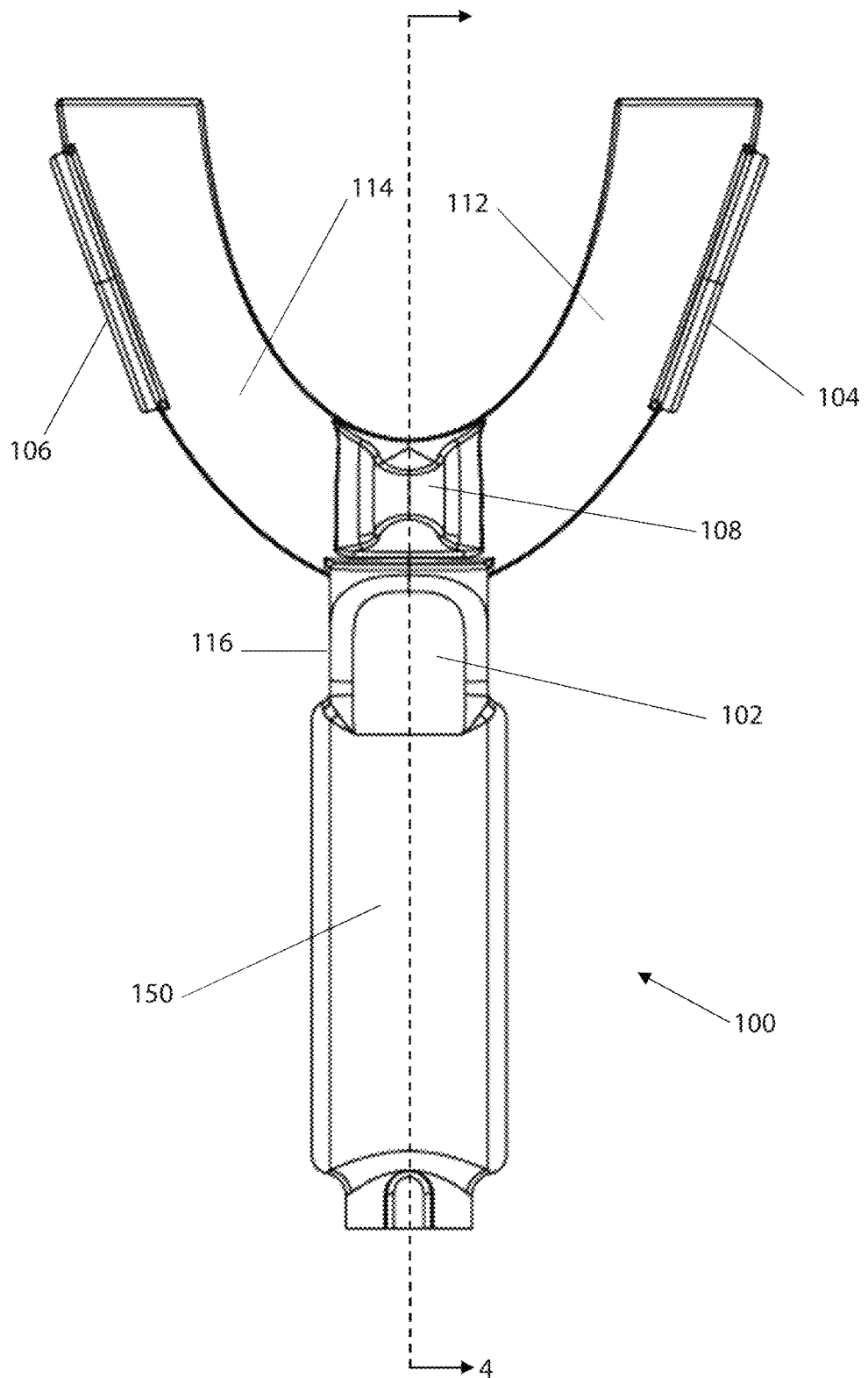
Figure 4D:
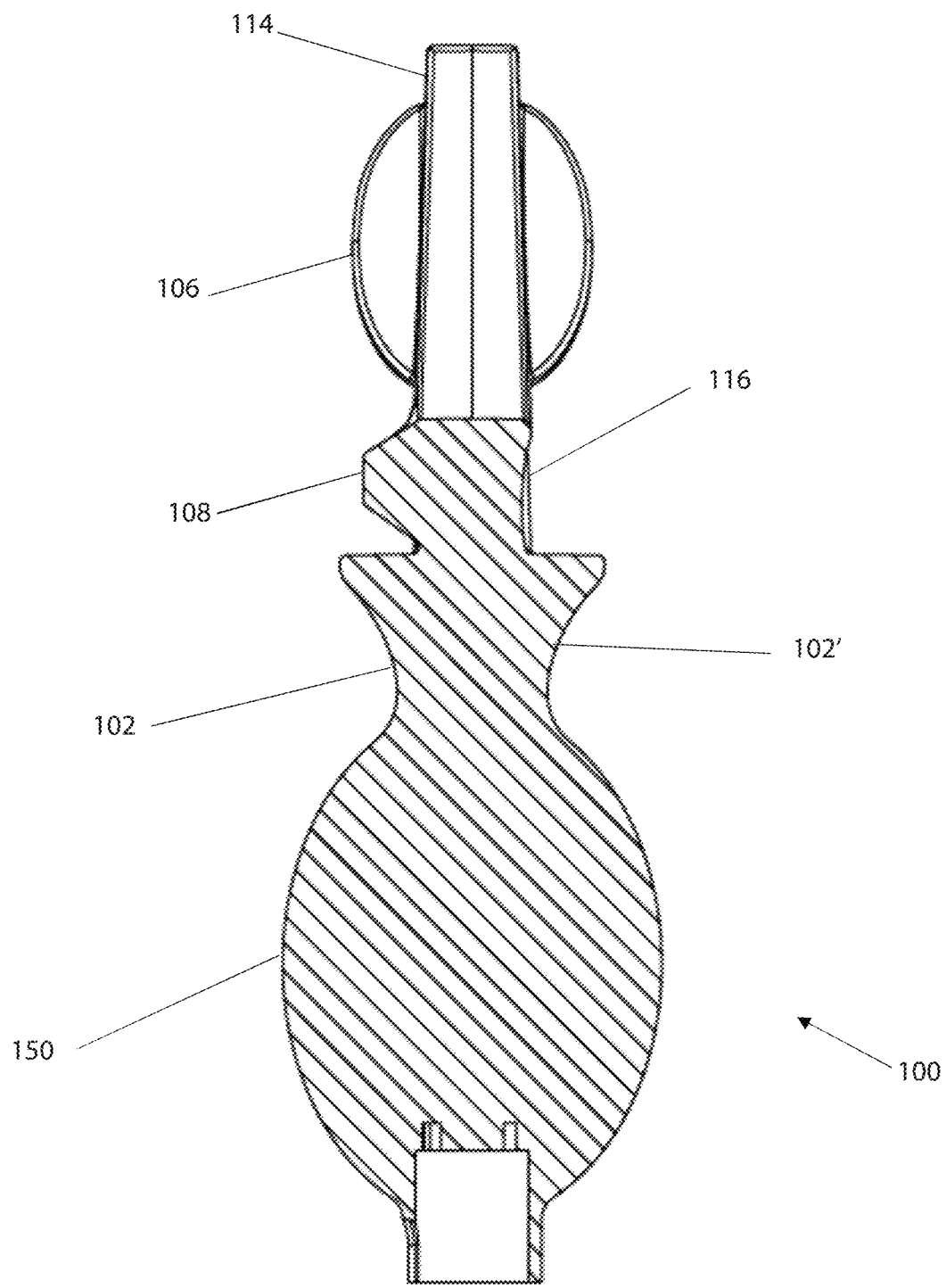
FIG. 4d is a cross sectional view taken along line 4-4 of the mouthpiece of FIG. 4c.

Reference is now made to FIG. 4b, which illustrates an alternative configuration of a mouthpiece 100'. The mouthpiece 100' has a tubing network 128' having two separate fluid cavities 132 and 134. Cavity 132 is provided in branch 112 and cavity 134 is provided in branch 114. Open ends 130' and 130'' of tubes 132 and 134 are respectively connected to inlets of sensors 152' and 152'' mounted on a printed circuit board (PCB) 154' housed in compartment 150. A female electrical connector 156' molded in sensor compartment 150 is also mounted on the PCB 154', to enable electrical digital communication between outputs from sensors 152' and 152'' and the control unit 200. Thereby, electrical signals from sensors 152', 152'' and memory 160 are separately addressable through interface PCB 154' by the control/display unit 200 through the digital communication link 220 (represented in FIG. 5) provided by electrical conductors in cable 20 via a male connector 22 (represented in FIG. 1) removably connectable to the female connector 156'.

Other fluid tubing network configurations may be contemplated for different applications. For example, to compare the force applied by the front teeth with that of the back teeth, the fluid tubing network includes a front cavity and symmetrical back cavities, which are fluidly coupled and connected to a single sensor. Alternatively, the front and back cavities are independent and connected to separate sensors. In another example, to measure a force applied by the posterior jaw, the fluid tubing network includes two symmetrical cavities, which are fluidly coupled and connected to a single sensor. In still another example, to measure a force applied by the anterior jaw, the fluid tubing network is similar to the one represented in FIG. 2a, but the branches 112 and 114 are shorter, being symmetrically truncated at their respective back ends 122 and 124. The symmetrically truncated branches 112 and 114 are fluidly coupled and connected to a single sensor as illustrated in FIG. 4a. Alternatively, the symmetrically truncated branches 112 and 114 are independent and connected to separate sensors as illustrated in FIG. 4b. In yet another example, to measure a force applied by a single tooth, the fluid tubing network includes a single cavity fluidly coupled and connected to a single sensor. In still another example, to measure a force applied by the left and right jaw side (e.g. to determine an occlusion balance), the fluid tubing network includes two cavities fluidly coupled and connected to two separate sensors.

Reference is now made to FIG. 5, which represents a schematic diagram of the intraoral force measuring system 10, including the mouthpiece 100 and the hand-held control/display unit 200. The configuration represented in FIG. 5 corresponds to a single cavity mouthpiece 100. The control/display unit 200 comprises a processing unit 210 (e.g. a programmable integrated microcontroller) executing software program(s) for operating the control/display unit 200. Power is provided to the control/display unit 200 by power supply 204 (e.g. a rechargeable battery pack). The power supply 204 powers the processing unit 210, as well as any other hardware components of the control/display unit 200 requiring power. User control is provided through the user interface 206, which comprises at least one switch to enable powering on and shutting down of the control/display unit 200 and system 10. Electrical power supply and digital communication is provided between the cavity mouthpiece 100 and the control/display unit 200 through the wired link 220 using the cable 20 (represented in FIG. 1) and connectors 24/256 and 22/156. More specifically, the power supply 204 powers components (e.g. sensor 152, memory 160) of the cavity mouthpiece 100 through the wired link 220. Furthermore, exchange of information (in the form of digital electrical signals) between the cavity mouthpiece 100 and the control/display unit 200 is performed through the wired link 220. More specifically, a pressure measured by the sensor 152 and information from the memory 160 are transmitted through the wired link 220 to the processing unit 210 for further processing. The wired link 220 is a bidirectional communication channel, allowing the processing unit 210 to transmit information for storage in memory 160, and optionally commands for controlling operations of the sensor 152. The control/display unit 200 further comprises memory 208, including for instance at least one of the following: Read Only Memory (ROM), Random Access Memory (RAM), non-volatile memory (e.g. for logging purposes). Part of the memory 208 (e.g. ROM and RAM) may be integrated to the processing unit 210. The control/display unit 200 also comprises a display 202 for displaying data generated by the processing unit 210 based on information transmitted by the mouthpiece 100. For instance, a pressure measured and transmitted by the mouthpiece 100 is converted by the processing unit 210 into a corresponding measured bite force, which is displayed on the display 202.

The measured pressure is transmitted through the wired link 220 in the form of a digital output signal generated by the sensor 152, which is received and converted into a digital value of the measured pressure by the processing unit 210. The processing unit 210 further processes the digital value of the measured pressure to calculate the corresponding bite force.

Figure 6A:
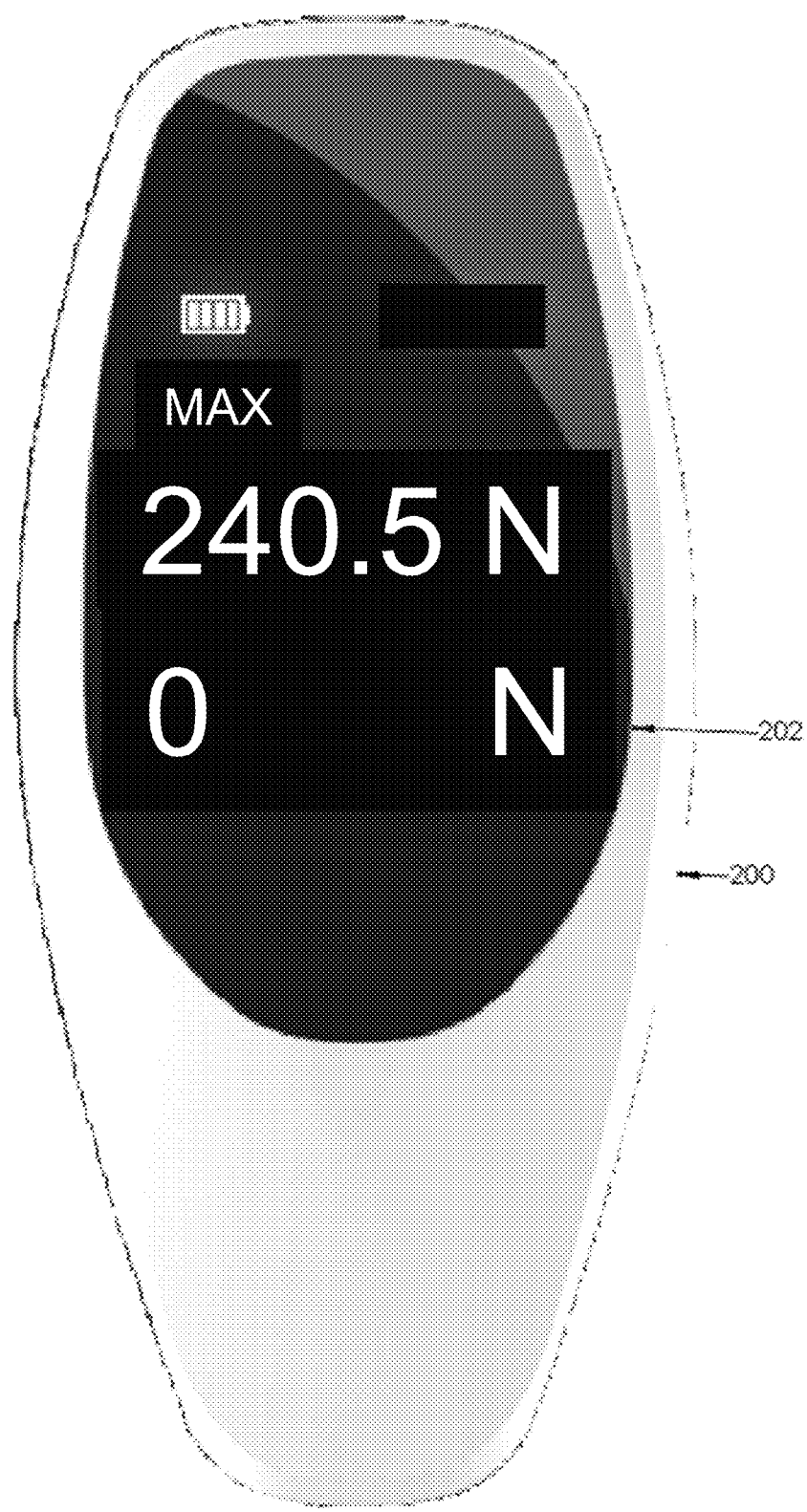

An exemplary representation of a calculated bite force on display 202 is illustrated in FIG. 6a. The bite force is expressed in Newtons (N). The maximum calculated bite force is displayed (1050 N in FIG. 6a), as well as the currently calculated bite force (0 N in FIG. 6a). Although not represented in FIG. 6a, the measured pressure may also be displayed on the display 202; for example, when operating in particular modes such as calibration, testing, debugging, etc. However, the measured pressure is not displayed in a standard operational mode with a patient.

In a particular implementation, the sensor 152 of the mouthpiece 100 measures and transmits a plurality of values of the pressure over a short interval of time (e.g. two seconds), in order to calculate a pressure value based on the plurality of transmitted values. The pressure value is calculated by the processing unit 210, taking into account all the transmitted values, or only a subset of the transmitted values. For example, five measured pressure values are transmitted by the sensor 152 and received by the processing unit 210. The pressure value is the average of the three highest values among the five transmitted values. A person skilled in the art will readily understand that various algorithms may be implemented for calculating an average value based on a subset of the transmitted values. The calculation of the pressure value based on several measured and transmitted values improves the accuracy of the mouthpiece 100.

In the case of a mouthpiece such as mouthpiece 100' (represented in FIG. 4b) comprising more than one sensing cavity connected to more than one pressure-sensing device, digital outputs therefrom (measured pressures) are received by the processing unit 210 along with information from memory 160 indicating that data for two (or more) pressure values are available to be read. The software program executed by the processing unit 210 performs accordingly. For example, the processing unit 210 converts the received digital outputs into digital values of the pressures measured by the two (or more) pressure-sensing devices. The information received from the memory 160 comprises data allowing identification of which pressure-sensing device transmitted which digital outputs. For example, the information received from the memory 160 comprises an identifier of a first pressure-sensing device which is present in the digital outputs transmitted by the first pressure-sensing device for identification purposes, and an identifier of a second pressure-sensing device which is present in the digital outputs transmitted by the second pressure-sensing device for identification purposes. Additionally, the software program executed by the processing unit 210 may also calculate a mean pressure value based on the respective pressure values of the two (or more) pressure-sensing devices. As mentioned previously, the software program executed by the processing unit 210 may also convert the pressure values of the two (or more) pressure-sensing devices and the mean pressure value into corresponding bite force values of the two (or more) pressure-sensing devices and a corresponding mean bite force value. At least some of the values calculated by the processing unit 210 are displayed on the display 202. Alternatively or complementarity to the determination of absolute values of the pressure and/or bite force for the two pressure-sensing devices, the processing unit 210 may also determine a relative measure of the pressure and/or bite force of one of the two pressure-sensing devices relatively to the other one of the two pressure-sensing devices. The relative measure can be expressed as a percentage. For example, pressure (or bite force) for left pressure-sensing device is 25% higher than pressure (or bite force) for right pressure-sensing device.

Figure 6B:
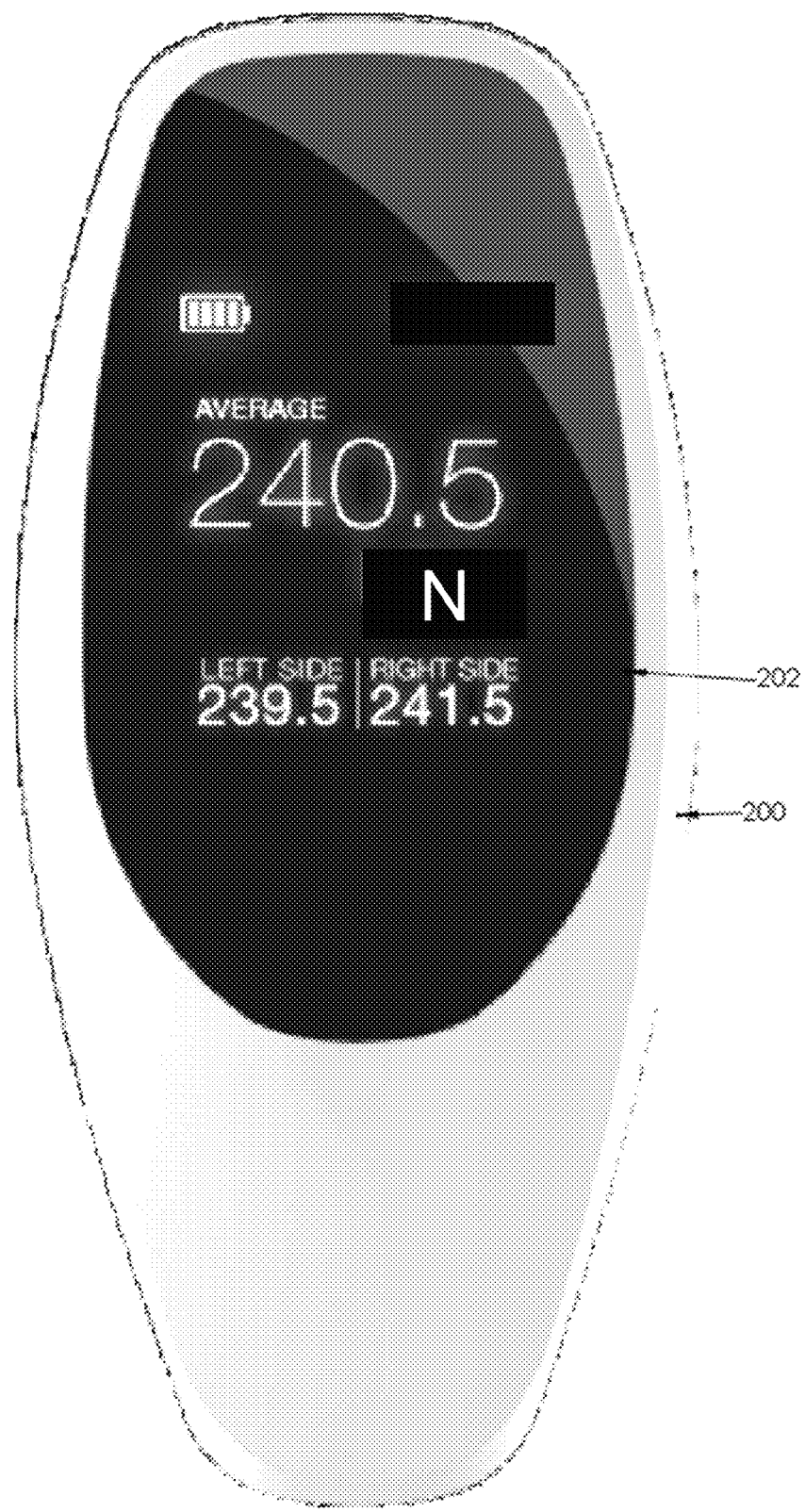
FIG. 6b represents a control/display unit of the system of FIG. 1, displaying information when using a dual-cavity mouthpiece according to FIG. 4b.

FIG. 6b shows exemplary information displayed on the display 202 when a dual cavity mouthpiece 100' is detected by the control/display unit 200. In the example provided in FIG. 6b, the measured bite force for each side (left and right sides) is respectively displayed, as well as a calculated mean bite force (the mean bite force is the average of the left side and right side measured bite forces, alternatively the mean bite force can be calculated based on the mean value of the left side pressure and the right side pressure). In the example illustrated in FIG. 6b, the left side measured bite force is 239.5 N, the right side measured bite force is 241.5 N, and the calculated mean bite force is 240.5 N.

The user interface 206 can be used to control which values are calculated by the processing unit 210 and displayed on the display 202 (e.g. pressure values only, bite force values only, a combination of bite force and pressure values, individual or mean values (or a combination thereof) in the case of a mouthpiece having two or more pressure-sensing devices).

The system 10 can be adapted to implement a compact power source in the compartment 150 to supply electrical power to the components therein (such as the pressure-sensing device 154, the memory 160, etc.). In this configuration, the electrical cable 20 can be replaced by a wireless data communication link, such as a Wi-Fi®, cellular (e.g. LTE®) or Bluetooth® connection. A wireless communication interface (not represented in the Figures) hosted by the PCB 154 is also powered by the compact power source in the compartment 150, and provides for exchanging information with the control/display unit 200.

The wireless communication interface (not represented in the Figures) hosted by the PCB 154 in the compartment 150 of the mouthpiece 100 can also be used for exchanging information with computing devices different from the control/display unit 200. For example, the wireless communication interface is used to transmit the pressure values measured by the pressure-sensing device(s) of the mouthpiece 100 to a computing device (e.g. a laptop, desktop, phone, watch, tablet, cloud service, etc. not represented in the Figures) storing a medical record of a patient being currently examined with the mouthpiece 100. The transmitted pressure values are added to the medical record of the patient. Furthermore, the computing device executes a computer program similar to the one executed by the processing unit 210 of the control/display unit 200. Thus, the computing device is capable of performing all the calculations performed by the processing unit 210 (e.g. conversion of a measured pressure value into a corresponding bite force value, calculation of a mean (and/or relative) pressure value or a mean (and/or relative) bite force value in the case of two or more pressure-sensing devices, etc.). The computing device further stores the calculated values in the medical record of the patient, and displays at least some of the calculated values on a display of the computing device.

Furthermore, in a previously mentioned configuration, the pressure-sensing device of the mouthpiece 100 measures and transmits in real time (via its wireless communication interface) a plurality of values of the pressure over a short interval of time. The computing device receives the plurality of values of the pressure and displays a curve representing the evolution of the value of the measured pressure (and/or the corresponding calculated value of the bite force) as a function of the time.

Figure 7:
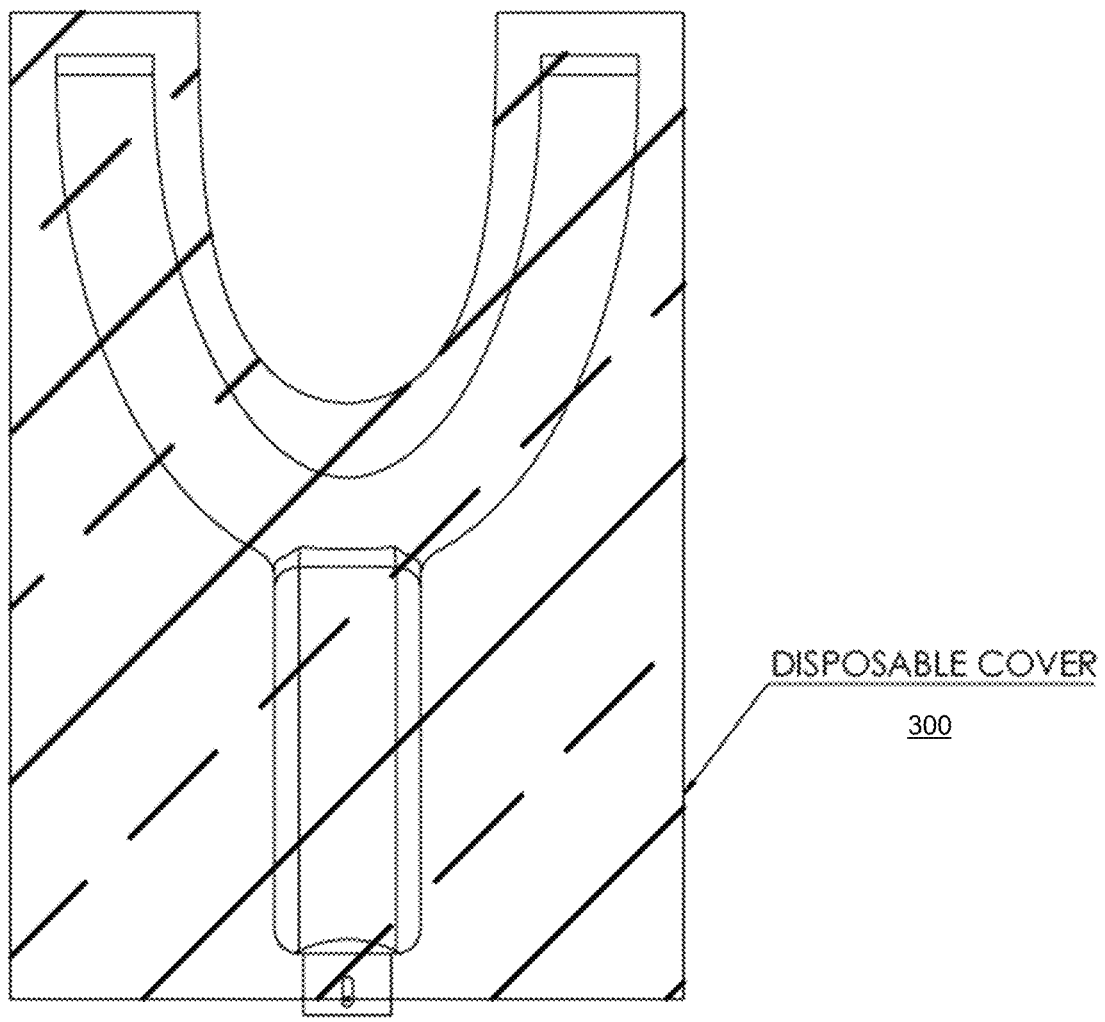
FIG. 7 is a perspective representation of a mouthpiece of the system of FIG. 1 in a ready-to-use state protected by a disposable shielding envelope.

Referring now to FIG. 7, a disposable shielding envelope 300 may be provided to cover the mouthpiece 100 prior to insertion into the intraoral cavity of an individual. Thereby, contact between the mouthpiece and fluids and microorganisms present in the intraoral cavity is efficiently prevented. The envelope 300 is made resistant to biting for a single patient use. At least one-millimeter thick heavy-duty polymer material has been found appropriate yet very cost-effective for this purpose, when compared to sterilization costs or disposable sensing mouthpieces. Polymeric material such as polyethylene or polypropylene can be used for that purpose.

Calibration Procedure

Referring now to FIGS. 1 and 5, a calibration procedure of the mouthpiece 100 will be described. As mentioned previously, the control/display unit 200 is capable of displaying on the display 202 at least one of the pressure measured by the pressure sensor 152 of the mouthpiece 100 and a bite force corresponding to the measured pressure. The displayed bite force corresponds to the force applied by the tooth/teeth of the patient on the mouthpiece 100, and shall be as accurate as possible. In order to perform an accurate conversion of the measured pressure into the corresponding bite force, calibration parameters are determined during a calibration phase of the mouthpiece 100. The calibration parameters take into account the specificities of each individual mouthpiece 100 (e.g. volume of the internal tubing network 128 represented in FIGS. 2b and 4a, upper surface of the body 110 represented in FIGS. 2a and 4a, etc.), electrical response to the applied pressure of the pressure sensor 152, potential minor manufacturing defaults of the mouthpiece 100, etc.).

During the calibration phase of the mouthpiece 100, the calibration parameters are determined, and then stored in the memory 160 of the mouthpiece 100. During the operational phase of the mouthpiece 100, the calibration parameters are transmitted to the control/display unit 200 and used by the processing unit 210 of the control/display unit 200 for calculating the bite force(s) corresponding to the pressure(s) measured and transmitted by the pressure sensor 152. The calibration parameters are transmitted once and stored in the memory 208 of the control/display unit 200. The calibration parameters currently stored in the memory 208 are used as long as the current mouthpiece 100 is interfaced with the control/display unit 200. Alternatively, the calibration parameters are transmitted from the memory 160 to the control/display unit 200 each time a new pressure is measured and transmitted by the pressure sensor 152.

Having the calibration parameters stored in the memory 160 of the mouthpiece 100 provides for automatically adapting the calculation of the bite force (corresponding to a pressure measured by the sensor 152) to the unique characteristics of the mouthpiece 100 currently interfaced to the control/display unit 200. Thus, an operator of the control/display unit 200 can easily change the mouthpiece 100 used with the control/display unit 200, without requiring manual configuration operations, since the adaptation is automatic and relies on the stored calibration parameters.

In an exemplary implementation of the mouthpiece 100, the correlation between the bite force applied by the teeth on the body 110 and the bite force measured by the system 10 is a N degree polynomial equation. For example, the correlation is a second (2) degree polynomial equation; and three calibration parameters a, b and c are stored in the memory 160. The bite force $F_{cal}$ corresponding to the pressure (x) measured and transmitted by the sensor 152 is calculated as follows: $F_{cal}=ax^2+bx^1+c$.

During the calibration phase, a load (calibrated load cell) is positioned on a specifically designed tool on the body 110 (represented in FIGS. 2a and 4a) of the mouthpiece 100. A pressure generated by the load is measured by the sensor 152 of the mouthpiece 100 and the load cell. The force applied by the load on the mouthpiece 100 is compared with the calibrated load cell, knowing the characteristics of the load (weight of the load, area of the surface of the load in contact with the mouthpiece, etc.). The operation is repeated with several different loads, and the calibration parameters are inferred based on the plurality of couples of known force and corresponding measured pressure. Depending on the complexity of the mathematical formula for calculating the bite force corresponding to a measured pressure based on the calibration parameters, different algorithms can be used for inferring the calibration parameters based on the data (couples of known force and corresponding measured pressure) collected during the calibration phase.

Referring to the aforementioned exemplary implementation where $F_{cal}=ax^2+bx^1+c$ ($2^{nd}$ degree polynomial equation), the calibration parameters a, b and c can be determined with a plurality of couples of known force and corresponding measured pressure. For example, a first load generates a force $x=X_1$ and a corresponding pressure $F_{cal,1}$ is measured by sensor 152, where $F_{cal,1}=ax^2+bx^1+c$. A second load generates a force $x=X_2$ and a corresponding pressure $F_{cal,2}$ is measured by sensor 152, where $F_{cal,2}=ax^2+bx^1+c$. The same calibration process is applied for each of the couples of known force and corresponding pressure. Then, the calibration parameters a, b and c are determined based on these couples of known force and corresponding measured pressure, by optimizing the polynomial fit to the $F_{cal}$ values obtained by comparing the load applied on the calibrated load cell and the resulting value measured by the mouthpiece, as is well known in the art of polynomial algebra.

More generally, if the correlation is a N degree polynomial equation, then up to N+1 coefficients (a, b, c, d, etc.) of the polynomial equation $F_{cal}=ax^N+bx^{N-1}+cx^{N-2}+dx^{N-3}+$etc. need to be determined during the calibration procedure. The calibration process for determining the coefficients is the same as the one previously described for the exemplary $2^{nd}$ degree polynomial equation.

Furthermore, the degree N of the polynomial equation may not be fixed in advance. In this case, a polynomial regression using the couples of known force and corresponding pressure can be used for determining the most accurate N degree polynomial equation, as is well known in the art of polynomial algebra.

During the calibration phase, the mouthpiece 100 is interfaced to a computing device executing a calibration algorithm. For instance, the computing device executing the calibration algorithm is the control/display unit 200. Alternatively, the computing device executing the calibration algorithm is a computer, a laptop, a tablet, etc. In the case where the calibration algorithm is executed by the control/display unit 200, the known forces are provided to the control/display unit 200 via its user interface 206. The corresponding pressures measured by the sensor 152 are directly transmitted by the mouthpiece 100 to the control/display unit 200. The processing unit 210 of the control/display unit 200 executes the calibration algorithm to infer the calibration parameters based on the received couples of known force and corresponding measured pressure. The inferred calibration parameters are transmitted to the mouthpiece 100 for storage in the memory 160.

Figure 8:
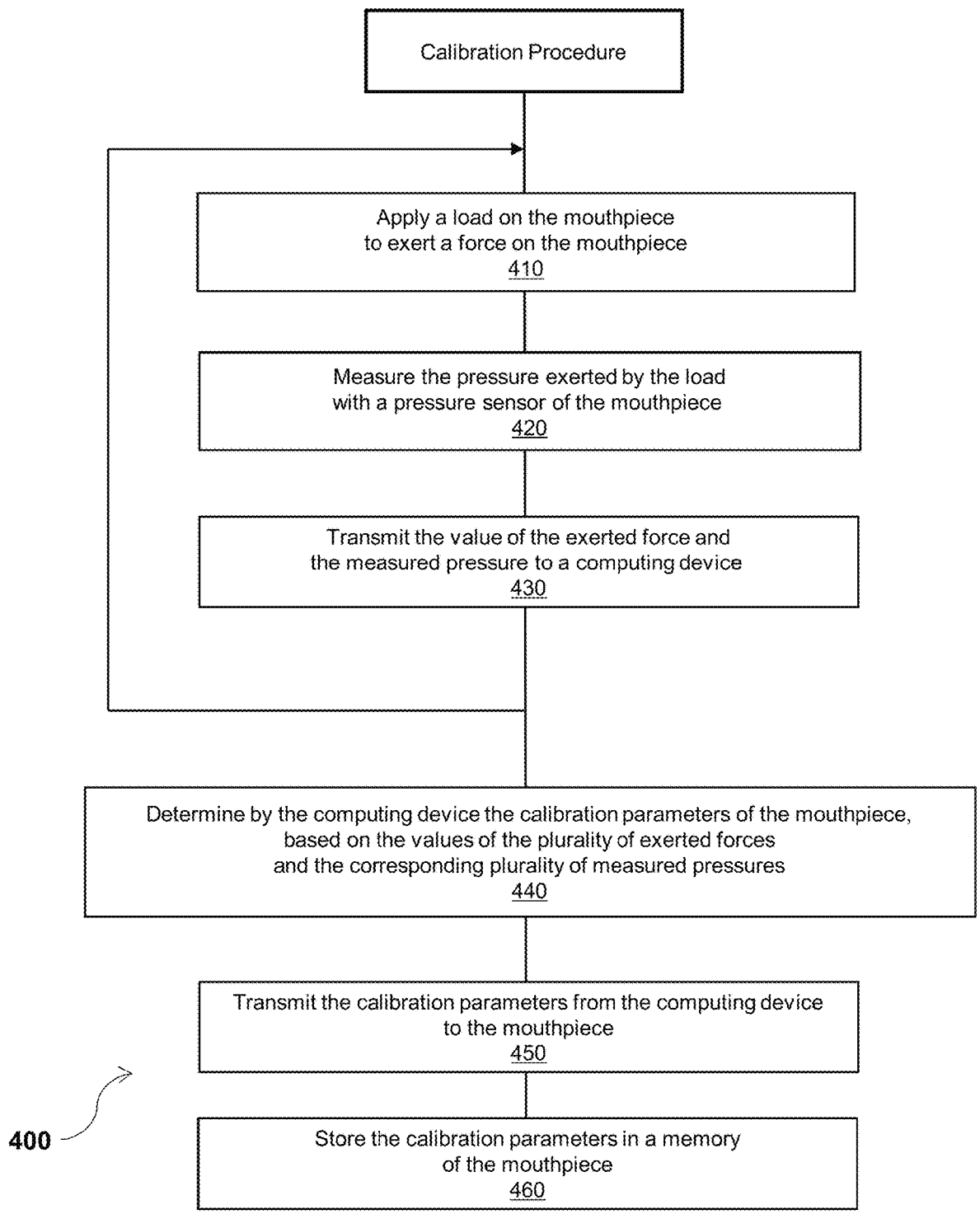
FIG. 8 illustrates a method for calibrating the mouthpiece represented in the previous Figures.

Reference is now made to FIGS. 1, 5 and 8, where FIG. 8 represents a method 400 for calibrating the mouthpiece 100. The method 400 has been tested experimentally, and the mouthpieces 100 calibrated with the method 400 are compliant with pre-defined quality requirements. The pre-defined quality requirements ensure the accuracy and repeatability of measurements of an applied bite force performed with a calibrated mouthpiece 100.

The method 400 comprises the step 410 of applying a load on the mouthpiece 100 to exert a force on the mouthpiece 100. More specifically, the load is applied on the body 110 of the mouthpiece 100. For example, a specially designed jig is used for applying the load.

In an experimental setup, a pneumatic press is used for applying the load on the body 110 of the mouthpiece 100. The pneumatic press comprises two horizontal plates, at least one of the plates being movable vertically towards the other plate. The mouthpiece 100 is secured to one of the plates and the jig is secured to the other plate. By moving vertically one plate towards the other one, the jig applies a load on the body 110 of the mouthpiece 100 to exert the force. A user of the pneumatic press configures the pneumatic press to exert a given value of the force relevant to the calibration procedure.

The method 400 comprises the step 420 of measuring the pressure exerted by the load with the pressure sensor 152 of the mouthpiece 100.

The method 400 comprises the step 430 of transmitting the measured pressure and the value of the exerted force to a computing device. For example, the computing device is connected to the mouthpiece 100 via a cable connected to the electrical connector 156. The pneumatic press comprises communication means (wired or wireless) for transmitting the exerted force to the computing device.

Various types of computing devices can be used, such as a laptop, a desktop, a tablet, etc. The computing device comprises adequate communication means for exchanging data with the mouthpiece 100; and for receiving data from the pneumatic press. The computing device also comprises a processing unit with sufficient processing capacity for performing the calculations of step 430.

Steps 410, 420 and 430 are repeated several times, to exert different values of the force on the mouthpiece; and to measure the corresponding pressures.

The method 400 comprises the step 440 of determining by the processing unit of the computing device the calibration parameters of the mouthpiece 100, based on the values of the plurality of exerted forces and the corresponding plurality of measured pressures. As mentioned previously, the calibration parameters are used by the control unit 200 (during an operational phase, after the calibration has been successfully performed) for the calculation of the bite force corresponding to the pressure measured by the mouthpiece 100.

An example of determination of the calibration parameters when the correlation between the exerted force and the measured pressure is a polynomial equation of degree N has been detailed previously.

The method 400 comprises the step 450 of transmitting the calibration parameters from the computing device to the mouthpiece 100.

The method 400 comprises the step 460 of storing the calibration parameters in the memory 160 of the mouthpiece 100.

The method 400 can be applied a first time to determine a first set of calibration parameters; and a second time to determine a second set of calibration parameters. The first and second sets of calibration parameters are used to calculate a plurality of bite forces corresponding to a plurality of measured pressures. If the variation of the bite forces when calculated with the first and second sets of calibration parameters is within a predefined range (e.g. predefined percentage of deviation), then the calibration is considered successful. One of the two sets of calibration parameters can be stored in the memory 160 of the mouthpiece 100. This validation procedure is used to ensure a satisfying accuracy of the measurements of an applied bite force with the mouthpiece 100.

Referring now concurrently to FIGS. 4b and 5, in the case of a mouthpiece 100' with a tubing network 128' having a plurality of separate fluid cavities (e.g. two fluid cavities 132 and 134) and a corresponding plurality of pressure sensors (e.g. two pressure sensors 152' and 152''), a unique set of calibration parameters is determined and stored in memory 160 for each one of the plurality of pressure sensors measuring the pressure of a corresponding fluid cavity. The unique set of calibration parameters associated to a given pressure sensor among the plurality of pressure sensors is used by the control/display unit 200 for calculating the bite force corresponding to the pressure measured by the given pressure sensor. The method 400 can be applied individually to each one of the plurality of separate fluid cavities, to determine a corresponding plurality of unique sets of calibration parameters.

The bite force measurement system of the present disclosure provides several advantages. For instance, implementation of the pressure sensor directly into the self-contained reusable mouthpiece makes the system less cumbersome and more cost-effective. Furthermore, features of the mouthpiece such as shape, material and structure contribute to improve comfort for the patient, provide accuracy and repeatability of the measurements, as well as cost-effective production and operation of the mouthpiece. Additionally, the storage of calibration parameters in the mouthpieces provides an automatic adaptation of a given mouthpiece to any control/display unit to which it is interfaced, by using the stored calibration parameters for calculating a bite force corresponding to a measured pressure.

Although the force measurement system of the present disclosure has been represented and described in the context of the measurement of a bite force, a person skilled in the art will readily recognize that the system can be adapted for the measurement of other intraoral forces and pressures relative to dental occlusion, mastication, tongue or cheek muscles strength, etc.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A bite force measuring system comprising:
   a mouthpiece adapted for being interfaced with a control unit, the mouthpiece comprising:
      a body defining first and second branches intersecting at a fore end and having a concave cross-section to mate with an individual's dental occlusion, the body forming a generally horseshoe shaped member, a thickness of the first and second branches increasing from respective back ends of the first and second branches towards the fore end;
      memory for storing calibration parameters;

a fluid-filled compressible cavity comprised in the body;

a fluid-pressure-sensing device for measuring a pressure of a fluid contained in the fluid-filled compressible cavity; and a communication interface for transmitting the calibration parameters and the measured pressure to the control unit; and the control unit comprising:

a communication interface for receiving the calibration parameters and the measured pressure from the mouthpiece; and a processing unit using the calibration parameters and the measured pressure for calculating a bite force corresponding to the measured pressure.

2. The bite force measuring system of claim 1, wherein the calibration parameters consist of coefficients of a polynomial equation of degree N with N greater or equal than 1, the bite force corresponding to the measured pressure being calculated by applying the polynomial equation to the measured pressure.

3. The bite force measuring system of claim 2, wherein the polynomial equation is of degree 2 and the calibration parameters consist of three coefficients a, b, and c; the bite force Fcai corresponding to the measured pressure x being calculated as follows: $F_{cal}=ax^2+bx^1+c$.

4. The bite force measuring system of claim 1, wherein the communication interface of the mouthpiece consists of one of the following: a wired communication interface, and a wireless communication interface.

5. The bite force measuring system of claim 1, wherein the pressure of the fluid contained in the fluid-filled compressible cavity is applied at an inlet of the fluid-pressure-sensing device, and an electrical signal representative of the pressure measured by the fluid-pressure-sensing device is generated at an output of the fluid-pressure-sensing device.

6. The bite force measuring system of claim 1, wherein the body has a Shore A hardness factor between 20 and 80.

7. The bite force measuring system of claim 1, wherein the body is molded from one of the following: a silicone based elastomeric material, and a flexible plastic.

8. The bite force measuring system of claim 1, wherein the mouthpiece further comprises a first guide for positioning the lips of a patient and including an extension located at the top of the fore end and an extension located at the bottom of the fore end; and two additional guides respectively symmetrically secured to an external surface of the first and second branches in proximity of respective back ends of the first and second branches, the two additional guides extending vertically.

9. The bite force measuring system of claim 8, wherein the mouthpiece further comprises a fourth guide located on top of the intersection of the first and second branches, the extension of the first guide located on top of the fore end and the fourth guide providing for positioning and blocking incisors of the patient.

10. The bite force measuring system of claim 1, wherein the memory of the mouthpiece further stores a number of measurement cycles of the mouthpiece, the number of measurement cycles corresponding to a number of calculations of the bite force performed by the processing unit of the control unit.

11. The bite force measuring system of claim 1, wherein the mouthpiece further comprises another separate fluid-filled compressible cavity and another fluid-pressure-sensing device for measuring a pressure of a fluid contained in the other fluid-filled compressible cavity, the memory of the mouthpiece storing other calibration parameters associated to the other fluid-filled compressible cavity, the other calibration parameters and measured pressure of the fluid contained in the other fluid-filled compressible cavity being transmitted from the mouthpiece to the control unit and used by the processing unit of the control unit for calculating a corresponding bite force.

12. The bite force measuring system of claim 1, wherein the control unit further comprises a display for displaying at least one of the following: the measured pressure, and the calculated bite force.

13. The bite force measuring system of claim 1, wherein the processing unit of the control unit calculates a pressure consisting of an average of a plurality of measured pressures received from the mouthpiece, the calculation of the bite force using the calibration parameters and the calculated pressure.

14. A method for calibrating a mouthpiece comprising a body, the body comprising a fluid-filled compressible cavity, the method comprising:

repeating the following steps a plurality of times:

applying a load on the body of the mouthpiece to exert a force on a fluid contained in the fluid-filled compressible cavity;

measuring by a fluid-pressure-sensing device of the mouthpiece a pressure of the fluid contained in the fluid-filled compressible cavity; and transmitting the value of the exerted force and the measured pressure to a computing device;

determining by a processing unit of the computing device calibration parameters of the mouthpiece based on the values of the plurality of exerted forces and the corresponding plurality of measured pressures, the calibration parameters allowing the calculation of a bite force based on the calibration parameters and a corresponding measured pressure;

transmitting the calibration parameters from the computing device to the mouthpiece; and storing the calibration parameters in a memory of the mouthpiece;

wherein the body of the mouthpiece defines first and second branches intersecting at a fore end and having a concave cross-section to mate with an individual's dental occlusion, the body forming a generally horseshoe shaped member, a thickness of the first and second branches increasing from respective back ends of the first and second branches towards the fore end.

15. The method of claim 14, wherein the calibration parameters consist of coefficients of a polynomial equation of degree N with N greater or equal than 1, the bite force corresponding to the measured pressure being calculated by applying the polynomial equation to the measured pressure.

16. The method of claim 15, wherein the polynomial equation is of degree 2 and the calibration parameters consist of three coefficients a, b, and c; the bite force Fcai corresponding to the measured pressure x being calculated as follows: $F_{cal}=ax^2+bx^1+c$.

17. The method of claim 15, wherein the processing unit of the computing device determines the degree N of the polynomial equation by applying a polynomial regression to the values of the plurality of exerted forces and the corresponding plurality of measured pressures.

18. The method of claim 14, further comprising determining a second set of calibration parameters based on a second set of values for the plurality of exerted forces and the corresponding plurality of measured pressures; and using the second set of calibration parameters to evaluate an accuracy of the previously determined calibration parameters.

* * * * *